US009599543B2

(12) United States Patent
Ebrahim et al.

(10) Patent No.: US 9,599,543 B2
(45) Date of Patent: Mar. 21, 2017

(54) CUSTOMIZED QUALITY CONTROLS FOR ANALYTICAL ASSAYS

(71) Applicant: Bio-Rad Laboratories, Inc. QSD, Hercules, CA (US)

(72) Inventors: Alireza Ebrahim, Laguna Niguel, CA (US); Christopher Spates, Laguna Hills, CA (US); Karl De Vore, Coto de Caza, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 36 days.

(21) Appl. No.: 14/938,780

(22) Filed: Nov. 11, 2015

(65) Prior Publication Data

US 2016/0061694 A1 Mar. 3, 2016

Related U.S. Application Data

(62) Division of application No. 13/594,227, filed on Aug. 24, 2012, now abandoned.

(60) Provisional application No. 61/536,902, filed on Sep. 20, 2011.

(51) Int. Cl.
*G01N 33/00* (2006.01)
*G01N 1/28* (2006.01)
*G01N 33/96* (2006.01)
*C12Q 1/32* (2006.01)
*G01N 21/91* (2006.01)

(52) U.S. Cl.
CPC .............. *G01N 1/28* (2013.01); *C12Q 1/32* (2013.01); *G01N 33/96* (2013.01); *G01N 21/91* (2013.01); *G01N 2001/2893* (2013.01); *G01N 2496/00* (2013.01)

(58) Field of Classification Search
CPC ...................................... G01N 21/91
USPC ......................... 436/18; 252/408.1
See application file for complete search history.

(56) References Cited

U.S. PATENT DOCUMENTS

| 5,547,873 | A | 8/1996 | Magneson et al. |
| 5,747,268 | A | 5/1998 | Herring et al. |
| 6,194,394 | B1 | 2/2001 | Hawkins |
| 6,251,684 | B1* | 6/2001 | Buhl .................... A61K 9/1694 210/198.2 |
| 6,255,047 | B1 | 7/2001 | Toblesky et al. |
| 7,459,276 | B2 | 12/2008 | Cantor et al. |
| 7,588,942 | B2 | 9/2009 | Ho et al. |
| 2005/0014289 | A1 | 1/2005 | Parsons et al. |
| 2006/0068399 | A1 | 3/2006 | McMillan et al. |
| 2006/0154067 | A1* | 7/2006 | Cooper ...................... C08J 9/16 428/402 |
| 2006/0183681 | A1* | 8/2006 | Ebrahim ................ G01N 33/74 514/2.3 |
| 2007/0269839 | A1 | 11/2007 | Goertz et al. |
| 2008/0070324 | A1 | 3/2008 | Floyd et al. |
| 2009/0226416 | A1* | 9/2009 | Roschke ............ C07K 14/7158 424/130.1 |
| 2014/0329263 | A1 | 11/2014 | Ebrahim et al. |

FOREIGN PATENT DOCUMENTS

| CN | 1824802 A | | 8/2006 |
| JP | 2004-239880 A | | 8/2004 |
| JP | 2004239880 A | * | 8/2004 |

OTHER PUBLICATIONS

Analytical Control Systems, Inc. 2003. "Serum Controls." (5 pages).
Hycor Biomedical, Inc. 2010. "Hycor KOVA® urinalysis controls: let's talk consistency and accuracy." (1 page).
Sacks, "Performance Evaluation of Commercially Available Osmometer Control Solutions," retrieved online from http://www.aicompanies.com/documents/file/Control%20Solutions%20whitepaper2010-web.pdf, Advanced Instruments Incorporated, product catalog, 8 pages (2010).
International Search Report and Written Opinion for PCT/US2012/054103, mailed Nov. 23, 2012.
Extended European Search Report from EP Appl. No. 12834558.4, dated Feb. 12, 2015.
Notice of Reasons for Rejection from JP Appl. No. 2014-531852, dated Jan. 29, 2015.
Response dated Jan. 4, 2016, to Office Action of Oct. 1, 2015, in U.S. Appl. No. 14/270,701, filed May 6, 2014.
Office Action of Oct. 1, 2015, in U.S. Appl. No. 14/270,701, filed May 6, 2014.

* cited by examiner

*Primary Examiner* — Jill Warden
*Assistant Examiner* — Brittany Fisher
(74) *Attorney, Agent, or Firm* — Kilpatrick Townsend & Stockton LLP

(57) ABSTRACT

Solid beads each containing a selected quantity of analyte are combined and a liquid base matrix that contains attributes of a biological fluid that is to be assayed, together constitute a kit from which a laboratory technician can, at the point of use, prepare a liquid control for a particular analyte, and preferably a series of such controls at different levels of the same analyte customized for a particular assay.

16 Claims, No Drawings

CUSTOMIZED QUALITY CONTROLS FOR ANALYTICAL ASSAYS

CROSS-REFERENCE TO RELATED APPLICATION

This application is divisional of U.S. application Ser. No. 13/594,227, Aug. 24, 2012 and claims the benefit of provisional U.S. Application No. 61/536,902, filed Sep. 20, 2011, the contents of which are incorporated herein by reference in their entirety.

BACKGROUND OF THE INVENTION

1. Field of the Invention

This invention lies in the field of quality controls for assays of analytes in biological fluids.

2. Description of the Prior Art

Quality control materials are routinely used in clinical diagnostics laboratories to monitor the precision and accuracy of assay equipment, materials, and procedures with which assays are performed either manually or by automation. Examples of commonly assayed analytes are drugs, hormones, enzymes, and antibodies; others will be readily apparent to the experienced biochemist. Controls for assays of human samples are typically prepared by adding a known quantity of the target analyte to a processed human base matrix such as human serum or human urine since matrices such as these ensure that the controls are as sensitive to all anticipated analytical variances as the actual patient samples. Many of these controls are prepared in solid form by lyophilization of the fully constituted liquid, leaving the user with the simple task of rehydrating the solid by dissolving it in water.

Commercially available controls, whether for a single analyte or for multiple analytes, are commonly offered in bi-level or tri-level combinations to provide levels that are above, near, and below the medical decision point for each assay. Many of these controls are directed to groups of related analytes, such as tumor markers, for example, or analytes measured by one type of detection technology, such as routine chemistry analytes measured by photometry or urinalysis analytes measured by reflectance photometry using dry chemistry strips. In general, the controls are designed, developed, and optimized for use in certain common test methods and technologies and are often not useful for purposes that extend beyond these common uses, particularly purposes that entail different levels of concentration, different assay methodologies, and different reasons for conducting the assays.

Clinical diagnostic assays can differ in such factors as precision, accuracy, limits of quantitation, limits of detection, linearity, and reportable range, due to differences in assay architecture, detection technology, and source of supply of the assay. Assays for certain analytes lack standardization in such features as medical decision points, for example, and therefore the controls that are supplied with these assays are not fully interchangeable nor are they useful for quality control at detection levels that are outside the ranges spanned by the controls. Currently available assays for Troponin I, for example, are designed for decision points that vary from one supplier to the next by a factor as high as 4. Patient populations differ as well, and in some cases the decision points differ so much between populations that controls designed for one population are not suitable for another.

SUMMARY OF THE INVENTION

The present invention provides customizable quality controls that can be prepared by the user at the point of use and that enable the user to select the analyte(s) that the controls represent, the number of control levels, the concentration of analyte in each control, the base matrix, and other factors affecting the utility of the controls for particular assays. The invention thus resides in kits for the preparation of the controls, and in methods for preparing the controls. The kit materials consist of an aqueous liquid matrix and solid water-soluble beads containing the analyte(s). The term "bead" is used herein to denote spheres, pellets, or any solid bodies of similar size, i.e., capable of being packaged in a bottle, for example, and used either individually or in small quantities. In addition to the analyte, individual beads can contain a bulking agent to add structural integrity to each bead, plus other optional components to help control the characteristics and quality of the control as it is reconstituted. The aqueous liquid matrix, also referred to herein as a base matrix, is an aqueous solution of a salt and a buffer at a pH of about 4.0 to about 9.0, either in a human biological fluid or in water, and if in water, the solution preferably also contains human or animal source materials that provide the matrix with the attributes of a biological sample. The beads and the base matrix can be shipped and sold separately or as parts of a kit, and they can be combined at the site of use immediately prior to their use in testing the assay materials, equipment, or procedure, or combined by the purchaser and stored for later use. Uncombined, the beads and matrix can be shipped and stored without special maintenance conditions such as refrigeration or freezing.

These and other objects, features, and advantages of the invention are further explained below.

DETAILED DESCRIPTION OF THE INVENTION AND SELECTED EMBODIMENTS

The solid beads, which are soluble in water, can conveniently be manufactured as spheres, and the sizes of the spheres are not critical to the utility or novelty of the invention, and can vary. In many cases, spheres having diameters within the range of from about 3 mm to about 10 mm will be convenient to use. For controls to be used for single-analyte assays, each bead in certain embodiments of the invention will contain the single analyte as the only biologically derived species in the bead, and controls of different levels of concentration of that analyte can be obtained by dissolving different numbers of beads in separate and either equal or unequal volumes of base matrix. Controls within the scope of this invention can also be formulated for multi-component assays, i.e., assays for two or more analytes, either for simultaneous detection or in separate detections, by including the two or more analytes in the beads. Here as well, controls of different levels of concentration of both analytes can be obtained by dissolving different numbers of beads in different aliquots of the same volume of the base matrix. Controls for multi-component assays can also be prepared from beads with a single analyte per bead by combining beads of different analytes in a single volume of the base matrix, thereby allowing the user greater flexibility in the design and use of the controls. A set of different levels of each analyte can be achieved by using different numbers of beads in separate but equal volumes of the base matrix, or the same number of beads in different volumes of the base matrix.

The quantity of analyte per bead can vary widely and will be governed by the volume of the reconstituted control and the minimum number of beads to be used per control. For example, a given set of controls may include three levels of analyte, and the quantity of analyte in a single bead may thus be such that the control with the lowest analyte level can be achieved by reconstituting a single bead in a volume of base matrix. The number of levels that the user will prepare in forming the control set can also vary, and in some cases as little as two levels will suffice. In most cases, however, controls constituting three or more analyte levels will be prepared, thereby allowing the user to check for linearity of the assay response, and to have controls representing levels approximately equal to the decision point as well as above and below.

In certain embodiments of this invention, the beads will contain a single analyte and no additional species other than formulation adjuvants, which are materials included to dilute the concentration of the analyte in the bead or to enhance or modify the physical characteristics of the bead and the ability of the bead to dissolve or disperse rapidly in the base matrix. Formulation adjuvants may serve, for example, to maintain the physical integrity of the bead during storage, shipment, or handling, to impart chemical stability to the bead, the analyte, or both while still in bead form, to maintain the ionic strength or the pH of the reconstituted control once the bead is dissolved in the base matrix, or to give the reconstituted control the attributes of a human sample in any of various respects that do not interfere with the ability to detect the analyte. Certain beads may contain two or more analytes, although beads that are limited to a single analyte can offer greater flexibility in their use as they are reconstituted as controls, since controls with two or more analytes can be prepared by combining different beads with single analytes each, allowing the laboratory technician to control or vary the relative amounts. Optimal formulating adjuvants are those that do not interfere with the detection of the analytes in the reconstituted controls, by either masking the analytes, being detected in combination with the analytes in a manner that does not permit segregation of the detection of one analyte from another, or in any way affecting the sensitivity of the assay toward the analyte. Species that are best avoided in the beads include proteins and immunoglobulins other than the analyte.

One type of formulation adjuvant is a bulking agent. One or more bulking agents will provide physical integrity to the bead by helping the bead hold its shape. Conventional materials that are known to achieve this effect can be used. Examples of bulking agents are glycine, sorbitol, mannitol, lactose, dextrose, albumin, ovalbumin, gelatin, polysaccharides such as dextran, and hydrophilic polymers such as polyvinylpyrrolidone. Bovine serum albumin is particularly convenient in many cases. The appropriate volume of bulking agent will be readily apparent to those of skill in bead formulation, and actual values are not critical to the novelty or utility of the invention. When beads are formed by lyophilization of aqueous solutions, for example, the solution prior to lyophilization in many cases will contain from about 0.3 g to about 3 g of bulking agent per deciliter of solution.

Another type of formulation adjuvant is a salt, which can be included to maintain the ionic strength of the base matrix when the beads are dissolved in the matrix. The optimal quantity of salt in the bead will thus be that amount that will produce at most a minimal difference between the salt concentration of the base matrix and that of the reconstituted control. Again using as examples beads that are formed by lyophilization of aqueous solutions, the salt concentration of the aqueous bead solution prior to lyophilization may range from about 10 mM to about 300 mM. The salt itself can be any salt that is compatible with biological samples and that behaves in the same way in a control as it does in the sample to be assayed. Sodium chloride is a common salt for this type of use.

A third type of formulation adjuvant is a buffer to maintain the reconstituted control at a desired pH. The pH of the bead can vary widely as evidenced by the range quoted above, but for controls for typical assays of human and other mammalian subjects, the pH will generally range from neutral to slightly basic. In many cases, an optimal pH level will be within the range of from about 6.2 to about 8.5. Examples of suitable buffers are tris(hydroxymethyl)aminomethane (Tris base), tris(hydroxymethyl)aminomethane hydrochloride (Tris-HCl), bis(2-hydroxyethyl)iminotris-(hydroxymethyl)methane (Bis-Tris base), bis(2-hydroxyethyl)iminotris-(hydroxymethyl)methane hydrochloride (Bis-Tris-HCl), and N-2-hydroxyethyl-piperazine-N-2-ethanesulfonic acid (HEPES).

Beads for use in the present invention can be prepared by any conventional means, most convenient of which is by lyophilization from an aqueous solution in which the components of the ultimate bead are dissolved. The volume of the solution prior to freezing and sublimation can vary widely, although in most cases a volume ranging from about 5 μL to about 1,000 μL will provide the best results. Lyophilization avoids or minimizes degradation of the bead components due to exposure of the bead to elevated temperatures.

The human or biological source materials that are included in the base matrix in certain embodiments of this invention can be human serum albumin, bovine serum albumin, or any other albumin or protein in general that is analogous to human serum albumin. When human serum albumin or bovine serum albumin is also included in the bead(s) as a bulking agent, its concentration is preferably low enough that the dissolving of the bead in the base matrix does not result in a reconstituted control with a concentration that is substantially different from that of the base matrix prior to reconstitution. Thus, when the bulking agent in the bead is bovine serum albumin (BSA) and the additive in the base matrix is human serum albumin (HSA), the concentration of BSA in the aqueous solution from which the bead is formed (by lyophilization, for example) may be one-tenth to one-third, for example, of the concentration of HSA in the base matrix.

The base matrix can be provided with an osmolarity that provides a reconstituted control that most closely resembles the samples that are to be assayed. With these considerations in mind, osmolarity levels can vary widely, although in most cases best results will be achieved with an osmolarity within the range of from about 50 mOsm/kg to about 1,000 mOsm/kg. Osmolarity can be controlled by the inclusion of a salt, as in the beads themselves. The same types of salts can be used in both, again with sodium chloride as a convenient example. The base matrix can also be provided with a buffer, conveniently using the same buffer as in the beads.

The base matrix can also be prepared from human and animal source materials that have been treated to remove endogenous analytes that might interfere with particular assays. Examples of these source materials are human whole blood, plasma, serum, urine, and oral and synovial fluid. Endogenous analyte removal can be achieved by filtration, precipitation, decomposition by enzymatic and heat treatment, and chromatographic separations such as affinity separations, ion exchange, and size exclusion.

Further optional components of the base matrix are stabilizers and antimicrobial agents. Examples of stabilizers are protease inhibitors, chelating agents, cryoprotectants, reducing agents, crosslinking agents, and surfactants. Examples of antimicrobial agents are sodium azide, ciprofloxacin, chloramphenicol, gentamicin, amikacin, tobramycin, and amphotericin B. Appropriate amounts of these additives will be readily apparent to those of skill in their use.

EXAMPLE 1

Preparation of Beads

Single-analyte beads for five different analytes were prepared from aqueous solutions in which the concentration of analyte was 100 to 200 times higher than the target concentration of analyte in the reconstituted controls, to account for the dilution factors upon reconstitution. The formulations for various aqueous solutions used to prepare the beads are listed in Table I.

TABLE I

Bead Compositions Prior to Lyophilization

| Solution Component | Concentration in Solution |
|---|---|
| Analyte: Thyroxine: | |
| BSA | 1 g/dL |
| NaCl | 100 mM |
| HEPES | 20 mM |
| Thyroxine | 880 µg/dL |
| Analyte: Digoxin: | |
| BSA | 1 g/dL |
| NaCl | 100 mM |
| HEPES | 20 mM |
| Digoxin | 89.6 ng/mL |
| Analyte: Triglycerides: | |
| BSA | 1 g/dL |
| NaCl | 100 mM |
| HEPES | 20 mM |
| Triglycerides | 12,600 mg/dL |
| Analyte: Lactate Dehydrogenase (LDH): | |
| BSA | 1 g/dL |
| NaCl | 100 mM |
| HEPES | 20 mM |
| LDH | 19,600 U/L |
| Analyte: Prolactin: | |
| BSA | 1 g/dL |
| NaCl | 100 mM |
| HEPES | 20 mM |
| Prolactin | 856 ng/mL |

Twenty beads prepared from each solution were tested four times each for a total of eighty observations per analyte to determine bead-to-bead variability. The results are shown in Table II.

TABLE II

Single Analyte Bead Characteristics

| Analyte | Average Bead Diameter (mm) | Average Bead Mass (mg) | Average Analyte Content | Analyte Concentration Variation (coefficient of variation, %) |
|---|---|---|---|---|
| Thyroxine | 3.5 | 3.7 | 0.22 µg | 1.6 |
| Digoxin | 3.5 | 3.5 | 2.24 ng | 2.1 |
| Triglycerides | 5.0 | 13.0 | 3.15 mg | 2.0 |
| LDH | 3.5 | 3.4 | 0.49 U | 0.8 |
| Prolactin | 3.5 | 3.4 | 21.4 ng | 1.2 |

EXAMPLE 2

Preparation of Base Matrix

A base matrix was prepared by dissolving and mixing human serum albumin, NaCl, and HEPES buffer in water to achieve the concentrations listed in Table III.

TABLE III

Composition of the Base Matrix

| Component | Concentration |
|---|---|
| Human Serum Albumin | 5 g/dL |
| NaCl | 100 mM |
| HEPES | 20 mM |

Once the components were dissolved, the pH of the solution was adjusted to 7.8 using dilute HCl or NaOH. The solution was then aseptically filtered through a 0.2 µm membrane filter into 250-500 mL sterile polystyrene containers, filled and capped in small glass vials, 3 mL or 5 mL each, and stored at 2-8° C. to prevent microbial growth. The levels of the various analytes of Example 1 in the base matrix were then determined using commercially available assays and were found to be below the detection limits of the assays.

EXAMPLE 3

Preparation and Performance of the Controls

Customized controls were prepared by rehydrating selected numbers of analyte beads, each with a defined and assayed concentration, in a selected volume of the base matrix to achieve the desired concentration for each level of control. The recovery data for several tri-level single-analyte controls and one-multi-analyte control, all prepared at the point of use are listed in Table IV, showing the number of beads used for each control level, the volume of the base matrix used, and the resulting analyte concentrations for each control level.

TABLE IV

Detected Analyte Levels for Tri-Level Controls

| Level | Number of Beads | Volume of Base Matrix | Analyte Concentration | Assay Method |
|---|---|---|---|---|
| Analyte: Thyroxine | | | | |
| 1 | 1 | 3 mL | 5.18 µg/dL | ADVIA |
| 2 | 2 | 3 mL | 9.73 µg/dL | CENTAUR ® |
| 3 | 3 | 3 mL | 13.53 µg/dL | (Siemens) |
| Analyte: Digoxin | | | | |
| 1 | 2 | 5 mL | 0.89 ng/mL | ADVIA |
| 2 | 4 | 5 mL | 1.77 ng/mL | CENTAUR ® |
| 3 | 6 | 5 mL | 2.63 ng/mL | (Siemens) |
| Analyte: Triglycerides | | | | |
| 1 | 1 | 3 mL | 97.75 mg/dL | DIMENSION ® |
| 2 | 2 | 3 mL | 204.45 mg/dL | (Siemens) |
| 3 | 4 | 3 mL | 406.25 mg/dL | |
| Analyte: LDH | | | | |
| 1 | 1 | 5 mL | 95.0 U/L | DIMENSION ® |
| 2 | 2 | 5 mL | 194.5 U/L | (Siemens) |
| 3 | 4 | 5 mL | 375.5 U/L | |
| Analyte: Prolactin | | | | |
| 1 | 1 | 5 mL | 4.76 ng/mL | AxSYM |
| 2 | 3 | 5 mL | 13.41 ng/mL | (Abbott) |
| 3 | 6 | 5 mL | 24.68 ng/mL | |
| Analytes: Thyroxine/LDH/Prolactin | | | | |
| 1 | 1/2/3 | 5 mL | 4.9 µg/dL/96.9 U/L/4.8 ng/mL | |
| 2 | 1/2/4 | 5 mL | 9.1 µg/dL/192.0 U/L/14.0 ng/mL | |
| 3 | 1/3/6 | 5 mL | 12.9 µg/dL/373.0 U/L/26.9 ng/mL | |

Accelerated stability studies as a prediction of shelf life were conducted by storing vials of the unreconstituted beads at elevated temperatures of 35° C., 41° C., and 47° C. for 39 days, 22 days, and 13 days, respectively, which, assuming a 20 kcal/Mole activation, were all roughly equivalent to four years at 2-8° C. The beads were then reconstituted after the incubation periods at the elevated temperatures, and analyte concentrations/recoveries were then determined. The results are shown in Table V.

TABLE V

Accelerated Stability Studies

| Incubation Conditions | | Percent Analyte Recovery After Incubation | | | | |
|---|---|---|---|---|---|---|
| Temperature (° C.) | Period (days) | Thyroxine | Digoxin | LDH | Triglycerides | Prolactin |
| 35 | 39 | 102 | 102 | 101 | 100 | 100 |
| 41 | 22 | 100 | 97 | 102 | 98 | 101 |
| 47 | 13 | 97 | 95 | 99 | 98 | 95 |

Open-vial (in-use) stability studies were conducted by reconstituting beads and storing the vials containing the reconstituted beads in a refrigerator at 2-8° C. and removing them from the refrigerator daily for fourteen days, allowing them to equilibrate to room temperature for fifteen minutes, opening the vials and exposing their contents to the atmosphere, then closing them after thirty seconds to simulate a typical use, and returning them to the refrigerator at 2-8° C. Sample vials were stressed for fourteen days, and at the end of the study analyte recovery was compared to analyte recovery of freshly reconstituted beads tested at the same time. The results indicated that the analyte concentrations/activities varied by less than 10% from their original values over the fourteen-day period.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The term "consisting essentially of" when preceding the recitation of a species or a list of components is also intended to mean the addition of species or components other than those listed is optional and not excluded, but that such additional species or components, if present, are present either in trace amounts or in amounts so small that they do not affect the functionality of the invention. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A kit for preparation of a customized control for a diagnostic assay, said kit comprising:
   an aqueous liquid matrix comprising a salt and a buffer at a pH of from about 4.0 to about 9.0, wherein the aqueous liquid matrix comprises human or animal source materials from which endogenous species that interfere with the detection of said one or more selected analyte have been removed; and
   a plurality of solid water-soluble beads, wherein the solid water-soluble beads are prepared by lyophilization of an aqueous solution ranging in volume from about 5 µL to about 1,000 µL, and the solid water-soluble beads comprise at least one analyte, a bulking agent, a salt, and a buffer,
   wherein said beads are configured for 1) dissolving different quantities of the one or more solid water-soluble bead in separate aliquots of said aqueous liquid matrix, wherein the aliquots have equal volume; or 2) dissolving the same quantities of the one or more solid water-soluble bead in separate aliquots of said aqueous liquid matrix, wherein the aliquots have different volume.

2. The kit of claim 1 wherein said solid water-soluble beads consist essentially of one analyte, said bulking agent, said salt, and said buffer.

3. The kit of claim 1 wherein said kit comprising a plurality of distinct water-soluble beads, each distinct bead containing an analyte.

4. The kit of claim 1 wherein said assay is an assay of a plurality of distinct selected analytes, and each said water-soluble bead contains all of said analytes.

5. The kit of claim 1 wherein said aqueous liquid matrix further comprises a stabilizer selected from the group consisting of a protease inhibitor, a chelating agent, a cross-linking agent, a cryoprotectant, a reducing agent, and a surfactant.

6. The kit of claim 1 wherein said aqueous liquid matrix further comprises an antimicrobial agent selected from the group consisting of sodium azide, ciprofloxacin chloramphenicol, gentamicin, amikacin, tobramycin, and amphotericin B.

7. The kit of claim 1 wherein said aqueous liquid matrix has a pH of from about 6.2 to about 8.5.

8. The kit of claim 1 wherein said aqueous liquid matrix has an osmolarity of from about 50 to about 1,000 mOsm/kg.

9. The kit of claim 1 wherein each said water-soluble bead is substantially spherical with a diameter of from about 3 mm to about 10 mm.

10. The kit of claim 3 wherein at least one distinct water-soluble bead contains two or more analytes.

11. The kit of claim 1 wherein said human or animal source materials comprise a human biological fluid.

12. The kit of claim 1 wherein the aqueous liquid matrix comprises albumin.

13. The kit of claim 1, wherein the human or animal source materials is selected from the group consisting of whole blood, plasma, serum, urine, oral fluid, and synovial fluid.

14. The kit of claim 1, wherein the kit further comprises two or more aliquots of the aqueous liquid matrix having equal volume.

15. The kit of claim 1, wherein the kit further comprises two or more aliquots of the aqueous liquid matrix having different volume.

16. The kit of claim 12 wherein said albumin is selected from the group consisting of human serum albumin and bovine serum albumin.

* * * * *